US012569220B2

(12) United States Patent
Chung

(10) Patent No.: US 12,569,220 B2
(45) Date of Patent: Mar. 10, 2026

(54) BLOOD FLOW MEASUREMENT SYSTEM

(71) Applicant: EDGECARE INC., Seoul (KR)

(72) Inventor: Mann Sik Chung, Seoul (KR)

(73) Assignee: Edgecare Inc., Seoul (KR)

( * ) Notice: Subject to any disclaimer, the term of this patent is extended or adjusted under 35 U.S.C. 154(b) by 160 days.

(21) Appl. No.: 18/559,500

(22) PCT Filed: Jan. 16, 2023

(86) PCT No.: PCT/KR2023/000746
§ 371 (c)(1),
(2) Date: Nov. 7, 2023

(87) PCT Pub. No.: WO2024/029676
PCT Pub. Date: Feb. 8, 2024

(65) Prior Publication Data
US 2025/0099068 A1      Mar. 27, 2025

(30) Foreign Application Priority Data
Aug. 3, 2022     (KR) ........................ 10-2022-0096511

(51) Int. Cl.
*A61B 8/00*         (2006.01)
*A61B 8/06*         (2006.01)
*A61B 8/08*         (2006.01)
(52) U.S. Cl.
CPC .............. *A61B 8/06* (2013.01); *A61B 8/4477* (2013.01); *A61B 8/488* (2013.01); *A61B 8/54* (2013.01)
(58) Field of Classification Search
None
See application file for complete search history.

(56) References Cited

U.S. PATENT DOCUMENTS

2013/0338506 A1* 12/2013 Kim .................... G01S 7/52093
600/447
2021/0113194 A1* 4/2021 Padwal ................. G06T 7/0012

FOREIGN PATENT DOCUMENTS

KR      10-2010-0080533 A     7/2010
KR      10-2013-0139704 A     12/2013
KR      10-2015-0027482 A     3/2015
(Continued)

OTHER PUBLICATIONS

International Search Report for International Application No. PCT/KR2023/000746 dated May 3, 2023, ISA/KR.

*Primary Examiner* — Amal Aly Farag
(74) *Attorney, Agent, or Firm* — ArentFox Schiff LLP; Yun H. Choe

(57) ABSTRACT

The present disclosure is related to a blood flow measurement system containing, such as, a guide imaging probe, a first Doppler probe, a second Doppler probe, and a control unit, where the guide imaging probe includes a multiple imaging ultrasound elements disposed along a first direction, the first Doppler probe includes multiple first Doppler ultrasound elements disposed on one side of the guide imaging probe along a second direction corresponding to a direction perpendicular to the first direction, the second Doppler probe includes multiple second Doppler ultrasound elements disposed on the other side of the guide imaging probe along a third direction corresponding to a direction perpendicular to the first direction, and the control unit provides a control signal to control the guide imaging probe, the first Doppler probe, and the second Doppler probe.

9 Claims, 5 Drawing Sheets

(56) References Cited

FOREIGN PATENT DOCUMENTS

| KR | 10-2019-0044758 | A | 5/2019 |
| KR | 10-2470768 | B1 | 11/2022 |

* cited by examiner

| | ULTRASOUND TRANSMISSION | ULTRASOUND RECEPTION |
|---|---|---|
| BASIC MODE (BM) | GUIDE IMAGING PROBE | GUIDE IMAGING PROBE, FIRST AND SECOND DOPPLER PROBES |

FIG. 7
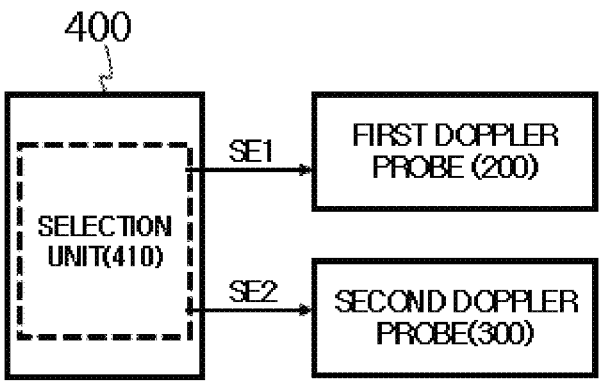
FIG. 8
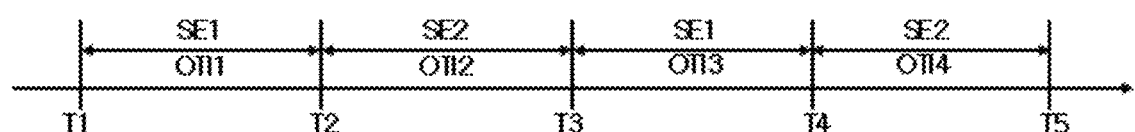
FIG. 9
OPERATION MODE (MD)
|  | ULTRASOUND TRANSMISSION |
|---|---|
| FIRST OPERATION MODE | GUIDE IMAGING PROBE |
| SECOND OPERATION MODE | FIRST DOPPLER PROBE, SECOND DOPPLER PROBE |

$$\theta_1 = \tan^{-1}\left(\cot\alpha - \frac{v_2}{v_1 \sin\alpha}\right)$$

$$\theta_2 = \pi - \alpha - \theta_1$$

$$V = \frac{v_1}{\cos\theta_1} = \frac{v_2}{\cos\theta_2}$$

NO DOPPLER INCIDENCE ANGLE EFFECT

BLOOD FLOW MEASUREMENT SYSTEM

CROSS-REFERENCE TO RELATED APPLICATION

This application is a 371 U.S. national stage of PCT/KR2023/000746, filed Jan. 16, 2023, which claims the benefit of Korean Patent Application No. 10-2022-0096511, filed Aug. 3, 2022, the contents of each of which are incorporated herein by reference.

TECHNICAL FIELD

The present invention relates to a blood flow measurement system.

BACKGROUND ART

The existing pulmonary artery catheter is a very invasive method, and therefore, has a risk of complications such as pulmonary artery rupture. Esophageal Doppler is minimally invasive and enables continuous blood flow measurement, but has the disadvantage of reducing reliability due to the absence of information on a tomographic area and a Doppler incidence angle. Recently, various studies are being conducted to solve this problem.

DISCLOSURE

Technical Problem

The present invention provides a blood flow measurement system capable of dramatically increasing pulse repetition frequency (PRF) for driving an ultrasound device by providing ultrasound signals transmitted from a guide imaging probe to an object, determining a location of a blood vessel based on ultrasound signals simultaneously received through the guide imaging probe, a first Doppler probe, and a second Doppler probe, and measuring a blood flow velocity.

Technical Solution

According to an embodiment of the present invention, a blood flow measurement system may include a guide imaging probe, a first Doppler probe, a second Doppler probe, and a control unit. The guide imaging probe may include a plurality of imaging ultrasound elements and may be disposed along a first direction. The first Doppler probe may include a plurality of first Doppler ultrasound elements and may be disposed on one side of the guide imaging probe along a second direction corresponding to a direction perpendicular to the first direction. The second Doppler probe may include a plurality of second Doppler ultrasound elements and may be disposed on the other side of the guide imaging probe along a third direction corresponding to a direction perpendicular to the first direction; The control unit may provide a control signal to control the guide imaging probe, the first Doppler probe, and the second Doppler probe.

The guide imaging probe may provide a transmitted ultrasound signal to an object based on a first control signal among the control signals provided by the control unit, and the guide imaging probe, the first Doppler probe, and the second Doppler probe may receive a received ultrasound signal reflected from the object.

The blood flow measurement system may further include a detection unit. The detection unit may detect location information of a blood vessel included in the object based on an image ultrasound reception signal received by the guide imaging probe among the received ultrasound signals.

The detection unit may further include a measurement unit. The measurement unit may measure a cross-sectional area corresponding to an area of a cross section of the blood vessel according to the location information of the blood vessel and a cross-section guide line formed in a depth direction of the ultrasound image.

The blood flow measurement system may further include a calculation unit. The calculation unit may calculate a blood flow velocity based on a first Doppler ultrasound reception signal received by the first Doppler probe among the received ultrasound signals and a second Doppler ultrasound reception signal received by the second Doppler probe among the received ultrasound signals.

The control unit may further include a selection unit. The selection unit may selectively drive the first Doppler probe and the second Doppler probe based on a selection signal among the control signals.

The selection unit may alternately drive the first Doppler probe and the second Doppler probe at driving intervals corresponding to a predetermined constant time interval.

The blood flow measurement system may operate in a plurality of operation modes. When the detection unit detects the location information of the blood vessel, in a first operation mode among the plurality of operation modes, the control unit may sequentially increase a transmission interval corresponding to an interval at which the transmitted ultrasound signal is transmitted.

When the detection unit detects the location information of the blood vessel, in a second operation mode among the plurality of operation modes, the control unit may drive the first Doppler probe and the second Doppler probe to alternately transmit a first Doppler ultrasound transmission signal and a second Doppler ultrasound transmission signal to the blood vessel included in the object.

The blood flow measurement system may calculate the blood flow velocity based on a first Doppler ultrasound reception signal received by the first Doppler probe by reflecting the first Doppler ultrasound transmission signal from the blood vessel and a second Doppler ultrasound reception signal received by the second Doppler probe by reflecting the second Doppler ultrasound transmission signal from the blood vessel.

In addition to the technical problems of the present invention described above, other features and advantages of the present invention will be described below, or may be clearly understood by those skilled in the art from such description and explanation.

Advantageous Effects

According to the present invention as described above, there are the following effects.

According to the present invention, a blood flow measurement system can dramatically increase pulse repetition frequency (PRF) for driving an ultrasound device by providing ultrasound signals transmitted from a guide imaging probe to an object, determining a location of a blood vessel based on ultrasound signals simultaneously received through the guide imaging probe, a first Doppler probe, and a second Doppler probe, and measuring a blood flow velocity.

In addition, other features and advantages of the present invention may be newly understood through the embodiments of the present invention.

BRIEF DESCRIPTION OF THE DRAWINGS

FIGS. 7 and 8 are diagrams for describing an operation of a selection unit included in a control unit of the blood flow measurement system of FIG. 1.

FIG. 9 is a diagram for describing a first operation mode and a second operation mode among the operation modes of the blood flow measurement system of FIG. 1.

BEST MODE

Figures 1, 2:
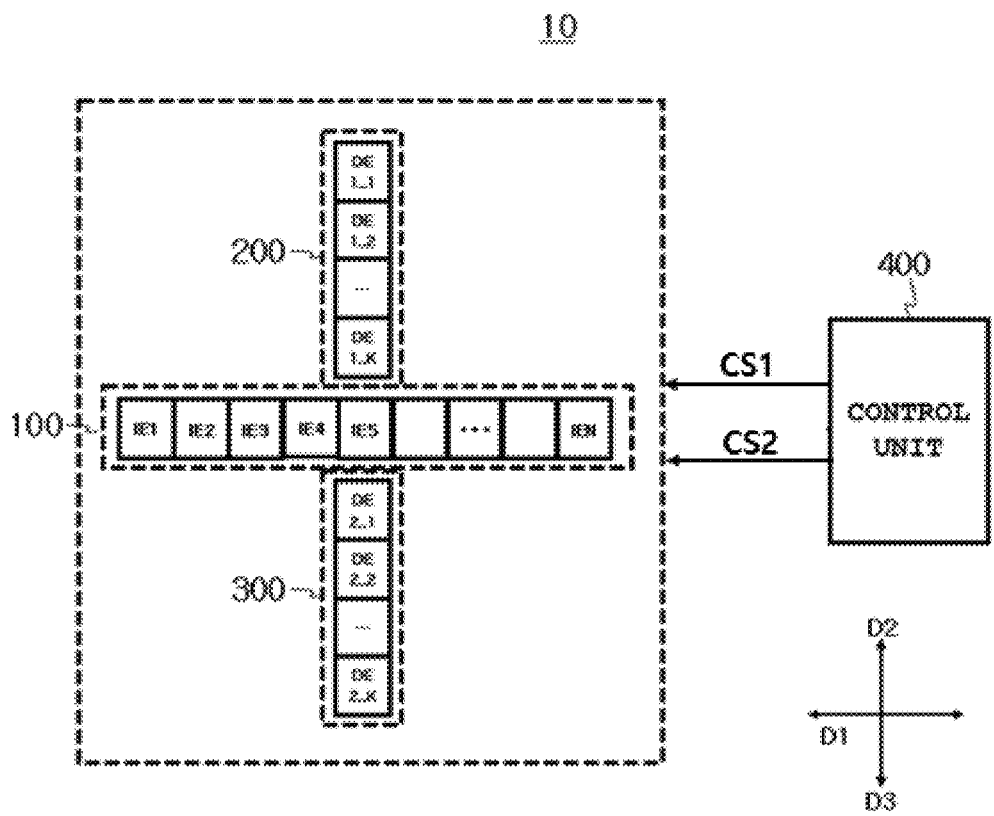
FIG. 1 is a block diagram illustrating a blood flow measurement system according to embodiments of the present invention.
FIG. 2 is a diagram for describing a basic mode among operation modes of the blood flow measurement system of FIG. 1.

In the specification, in adding reference numerals to components throughout the drawings, it is to be noted that like reference numerals designate like components even though components are shown in different drawings.

On the other hand, the meaning of the terms described in the present specification should be understood as follows.

Singular expressions should be understood as including plural expressions, unless the context clearly defines otherwise, and the scope of rights should not be limited by these terms.

Also, it should be understood that terms such as "include" and "have" do not preclude the existence or addition possibility of one or more other features or numbers, steps, operations, components, parts, or combinations thereof.

Hereinafter, preferred embodiments of the present invention designed to solve the above problems will be described in detail with reference to the accompanying drawings.

Figure 3:
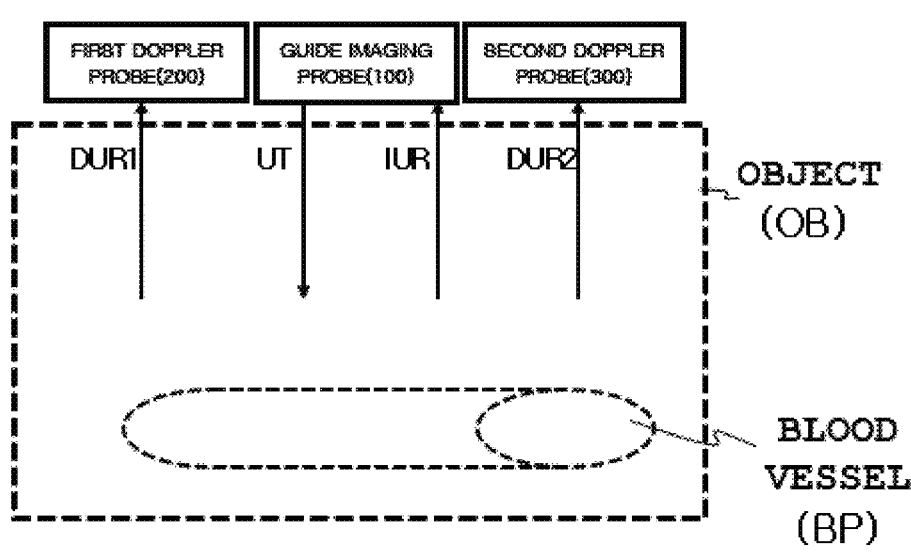
FIG. 3 is a diagram for describing operations of a guide imaging probe, a first Doppler probe, and a second Doppler probe included in the blood flow measurement system of FIG. 1.

FIG. 1 is a block diagram illustrating a blood flow measurement system according to embodiments of the present invention, FIG. 2 is a diagram for describing a basic mode among operation modes of the blood flow measurement system of FIG. 1, and FIG. 3 is a diagram for describing operations of a guide imaging probe, a first Doppler probe, and a second Doppler probe included in the blood flow measurement system of FIG. 1.

Referring to FIGS. 1 to 3, a blood flow measurement system 10 according to an embodiment of the present invention may include a guide imaging probe 100, a first Doppler probe 200, a second Doppler probe 300, and a control unit 400. The guide imaging probe 100 may include a plurality of imaging ultrasound elements and may be disposed along a first direction D1. For example, the first direction D1 may indicate left and right directions based on FIG. 1, and the imaging ultrasound elements may include a first imaging ultrasound element IE1 and a second imaging ultrasound element IE2 to an Nth imaging ultrasound element IEN. The blood flow measurement system 10 according to the present invention may transmit an ultrasound transmission signal UT to an object OB through the guide imaging probe 100, and implement an ultrasound image UI using an image ultrasound reception signal IUR reflected and received from the object OB. Here, the object OB may be a part of the human body.

The first Doppler probe 200 may include a plurality of first Doppler ultrasound elements and may be disposed on one side of the guide imaging probe 100 along a second direction D2 corresponding to a direction perpendicular to the first direction D1. For example, the first Doppler probe 200 may be disposed in the second direction D2 with respect to the guide imaging probe 100, and the first Doppler ultrasound elements may include a 1_1th Doppler ultrasound element DE1_1 and the 1_2th Doppler ultrasound element DE1_2 to a 1_Kth Doppler ultrasound element DE1_K. Here, K may be a natural number, and K may be the same as or different from the natural number N. The blood flow measurement system 10 according to the present invention may calculate a spectrogram indicating a first blood flow velocity of a blood vessel BP inside an object OB using a first Doppler ultrasound reception signal DUR1 reflected and received from the object OB through the first Doppler probe 200.

The second Doppler probe 300 may include a plurality of second Doppler ultrasound elements and may be disposed on the other side of the guide imaging probe 100 along a third direction D3 corresponding to a direction perpendicular to a first direction D1. For example, the second Doppler probe 300 may be disposed in a third direction D3 with respect to the guide imaging probe 100, and the second Doppler ultrasound elements may include a 2_1th Doppler ultrasound element DE2_1 and a 2_2th Doppler ultrasound element DE2_2 to a 2_Jth Doppler ultrasound element DE2_J. Here, J may be a natural number, and J may be the same as or different from the natural number N or K. The blood flow measurement system 10 according to the present invention may calculate a spectrogram indicating a second blood flow velocity of the blood vessel BP inside the object OB using a second Doppler ultrasound reception signal DUR2 reflected and received from the object OB through the second Doppler probe 300.

The control unit 400 may provide a control signal CS that controls the guide imaging probe 100, the first Doppler probe 200, and the second Doppler probe 300.

In one embodiment, after the guide imaging probe 100 provides a transmitted ultrasound signal UT to the object OB based on a first control signal CS1 among the control signals CS provided by the control unit 400, the guide imaging probe 100 may receive an image ultrasound reception signal IUR reflected from the object OB. Thereafter, the guide imaging probe 100 may provide the transmitted ultrasound signal UT to the object OB based on a second control signal CS2 among the control signals CS, and the first Doppler probe 200 and the second Doppler probe 300 may receive a Doppler ultrasound reception signal DUR reflected from the object OB. Here, the Doppler ultrasound reception signal DUR received by the first Doppler probe 200 may be a first Doppler ultrasound reception signal DUR1, and the Doppler ultrasound reception signal DUR received by the second Doppler probe 300 may be a second Doppler ultrasound reception signal DUR2. The blood flow measurement system 10 according to the present invention may determine location information PI of a blood vessel based on the image ultrasound reception signal IUR received by the guide imaging probe 100, and calculate a blood flow velocity BV based on the first Doppler ultrasound reception signal DUR1 and the second Doppler ultrasound reception signal DUR2 received by the first Doppler probe 200 and the second Doppler probe 300.

For example, the blood flow measurement system 10 according to the present invention may operate in multiple operation modes. In a basic mode BM among the plurality of operation modes, the guide imaging probe 100 may transmit the transmitted ultrasound signal UT to the object OB based on the first control signal CS1, and then receive the image ultrasound: reception signal IUR reflected from the object OB through the guide imaging probe 100. Thereafter, the guide imaging probe 100 may transmit the transmitted ultrasound signal UT to the object OB based on the second control signal CS2 among the control signals CS and receive the Doppler ultrasound reception signal reflected from the object OB through the first Doppler probe 200 and the second Doppler probe 300. The Doppler ultrasound reception signal DUR may include a first Doppler ultrasound reception signal DUR1 and a second Doppler ultrasound reception signal DUR2.

After the blood flow measurement system 10 according to the present invention transmits the transmitted ultrasound signal UT through the guide imaging probe 100 based on the first control signal CS1, and receives the image ultrasound reception signal IUR through the guide imaging probe 100, the blood flow measurement system 10 may repeatedly perform an operation of transmitting the transmitted ultrasound signal UT through the guide imaging probe 100 based on the second control signal CS2 and receiving the Doppler ultrasound reception signal DUR through the first Doppler probe 200 and the second Doppler probe 300 at predetermined regular time intervals.

In one embodiment, after the guide imaging probe 100 may provide the transmitted ultrasound signal UT to the object OB based on the second control signal CS2 among the control signals CS, the first Doppler probe 200 and the second Doppler probe 300 may receive the Doppler ultrasound reception signal DUR reflected from the object OB.

In another embodiment, after the first Doppler probe 200 and the second Doppler probe 300 provide the transmitted ultrasound signal UT to the object OB based on a third control signal CS3 among the control signals CS, the first Doppler probe 200 and the second Doppler probe 300 may receive the Doppler ultrasound reception signal DUR reflected from the object OB.

Figure 4:
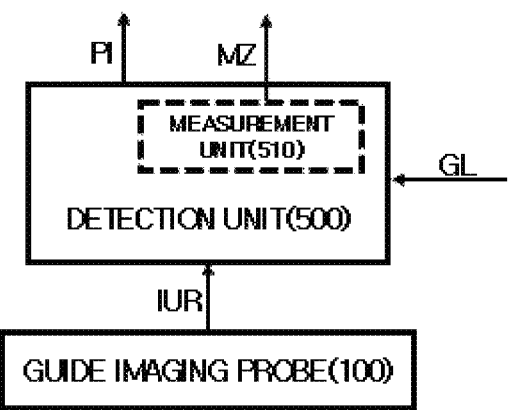
FIGS. 4 and 5 are diagrams for describing an operation of a detection unit included in the blood flow measurement system of FIG. 1.
Figure 5:
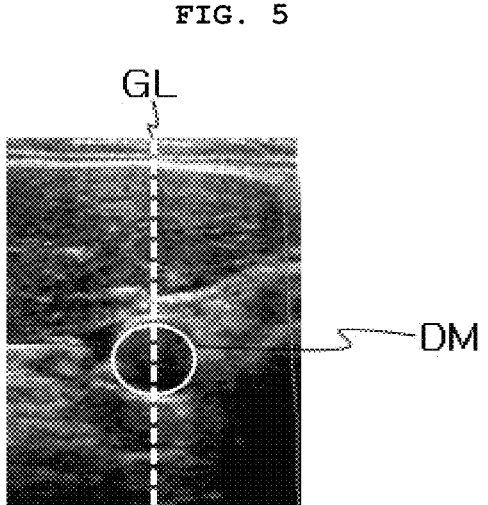

FIGS. 4 and 5 are diagrams for describing an operation of a detection unit included in the blood flow measurement system of FIG. 1.

Referring to FIGS. 1 to 5, in one embodiment, the blood flow measurement system 10 may further include a detection unit 500. The detection unit 500 may detect location information PI of the blood vessel BP included in the object OB based on the image ultrasound reception signal IUR received by the guide imaging probe 100 among the received ultrasound signals. For example, the blood flow measurement system 10 may provide the ultrasound image UI inside the object OB using the image ultrasound reception signal IUR received by the guide imaging probe 100. In this case, the detection unit 500 included in the blood flow measurement system 10 according to the present invention may check the location information PI of the blood vessel BP based on the ultrasound image UI.

In one embodiment, the detection unit 500 may further include a measurement unit 510. The measurement unit 510 may measure a cross-sectional area MZ corresponding to an area of a cross section of the blood vessel BP according to the location information PI of the blood vessel BP and a cross-section guide line GL formed in a depth direction of the ultrasound image. For example, the guide line GL may be a reference line that guides a cross section DM of the blood vessel BP to be disposed at the center of the ultrasound image UI. The measurement unit 510 included in the blood flow measurement system 10 according to the present invention may control the cross section DM of the blood vessel BP to be disposed on the guide line GL based on the position information PI of the blood vessel BP. Thereafter, the measurement unit 510 may measure a cross-sectional area MZ corresponding to the area of the cross-section DM of the blood vessel BP.

Figure 6:
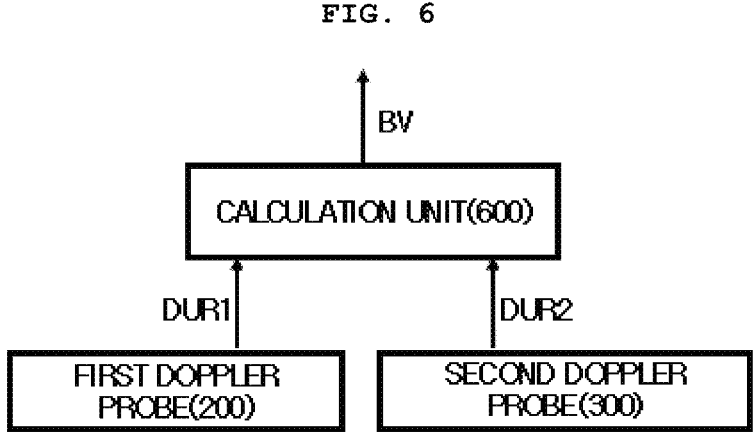
FIG. 6 is a diagram for describing an operation of a calculation unit included in the blood flow measurement system of FIG. 1.

FIG. 6 is a diagram for describing an operation of a calculation unit included in the blood flow measurement system in FIG. 1, and FIGS. 7 and 8 are diagrams for describing an operation of a selection unit included in the control unit of the blood flow measurement system in FIG. 1.

Referring to FIGS. 1 to 8, the blood flow measurement system 10 may further include a calculation unit 600. The calculation unit 600 may calculate the blood flow velocity based on the first Doppler ultrasound reception signal DUR1 received by the first Doppler probe 200 among the received ultrasound signals and the second Doppler ultrasound reception signal DUR2 received by the second Doppler probe 300 among the received ultrasound signals. In one embodiment, the control unit 400 may further include a selection unit 410. The selection unit 410 may selectively drive the first Doppler probe 200 and the second Doppler probe 300 based on a selection signal SE among the control signals CS. For example, the control signal CS may include the selection signal SE. The selection signal SE may include a first selection signal SE1 and a second selection signal SE2. To drive the first Doppler probe 200, the selection unit 410 may turn on the first selection signal SE1, and to drive the second Doppler probe 300, the selection unit 410 may turn on the second selection signal SE2.

In one embodiment, the selection unit 410 may alternately drive the first Doppler probe 200 and the second Doppler probe 300 at driving intervals corresponding to a predetermined constant time interval. For example, the plurality of times may include a first time T1 to a fifth time T5, and a driving interval OTI may include a first driving interval OTI1 to a fourth driving interval OTI4. The first driving interval OTI1 may be a time interval from the first time T1 to the second time T2, and the second driving interval OTI2 may be a time interval from the second time T2 to the third time T3. In addition, a third driving interval OTI3 may be a time interval from the third time T3 to a fourth time T4, and the fourth driving interval OTI4 may be a time interval from the fourth time T4 to a fifth time T5. In this case, the selection unit 410 may drive the first Doppler probe 200 by turning on the first selection signal SE1 during the first driving interval OTI1, and drive the second Doppler probe 300 by turning on the second selection signal SE2 during the second driving interval OTI2. In the same manner, the first Doppler probe 200 and the second Doppler probe 300 may be alternately driven during in the third driving interval OTI3 and the fourth driving interval OTI4.

Figure 10:
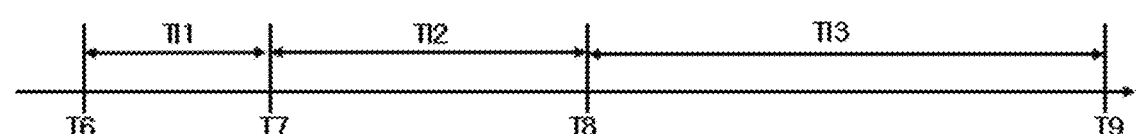
FIG. 10 is a diagram for describing the first operation mode of FIG. 9.
Figure 11:
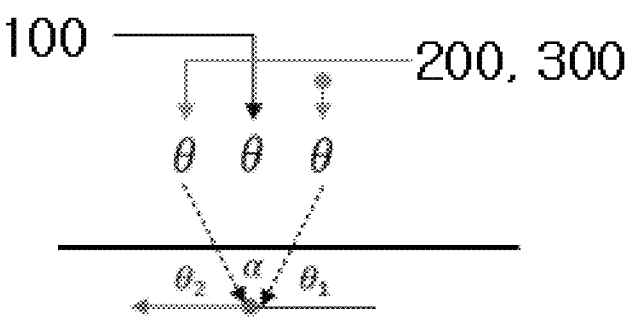
FIG. 11 is a diagram illustrating a method of calculating cardiac output by the blood flow measurement system of FIG. 1.

FIG. 9 is a diagram for describing a first operation mode and a second operation mode among the operation modes of the blood flow measurement system of FIG. 1, FIG. 10 is a diagram for describing the first operation mode of FIG. 9, and FIG. 11 is a diagram for describing a method of calculating cardiac output by the blood flow measurement system of FIG. 1.

Referring to FIGS. 1 to 11, the blood flow measurement system 10 may operate in a plurality of operation modes. When the detection unit 500 detects the location information PI of the blood vessel BP, in the first operation mode among the plurality of operation modes, the control unit 400 may sequentially increase a transmission interval corresponding to the interval at which the transmitted ultrasound signal UT is transmitted. For example, after the detection unit 500 accurately detects the location information PI of the blood vessel BP, in order to check the location of the internal blood vessel BP of the object OB, the detection unit 500 may not need to transmit the transmitted ultrasound signal UT as frequently as before detecting the location information PI of blood vessel BP.

In this case, the control unit 400 may sequentially increase the transmission interval. For example, the plurality of times may include a sixth time T6 to a ninth time T9. The transmission interval may include a first transmission interval TI1 to a third transmission interval TI3. The first transmission interval TI1 may be a time interval from the sixth time T6 to the seventh time T7, and the second transmission interval TI2 may be a time interval from the seventh time T7 to the eighth time T8. In addition, the third transmission interval TI3 may be a time interval from the eighth time T8 to the ninth time T9. In this case, the first transmission interval TI1 may be smaller than the second transmission interval TI2, and the second transmission interval TI2 may be smaller than the third transmission interval TI3. In this way, after the detection unit 500 detects the location information PI of the blood vessel BP, the detection unit 500 may gradually increase the time interval for implementing an ultrasound image using the guide imaging probe 100 to reduce a system load so that the blood flow measurement system 10 performs different operations.

The probe transmitting the ultrasound signal in the first operation mode may be the guide imaging probe 100, and the probe transmitting the ultrasound signal in the second operation mode may be the first Doppler probe 200 and the second Doppler probe 300.

In one embodiment, when the detection unit 500 detects the location information PI of blood vessel BP, in the second operation mode among the plurality of operation modes, the control unit 400 may drive the first Doppler probe 200 and the second Doppler probe 300 to alternately transmit the first Doppler ultrasound transmission signal and the second Doppler ultrasound transmission signal to the blood vessel BP included in the object OB. In addition, in one embodiment, the blood flow measurement system 10 may calculate the blood flow velocity based on the first Doppler ultrasound reception signal DUR1 received by the first Doppler probe 200 by reflecting the first Doppler ultrasound transmission signal from the blood vessel BP and a second Doppler ultrasound reception signal DUR2 received by the second Doppler probe 300 by reflecting the second Doppler ultrasound transmission signal from the blood vessel BP.

For example, after the detection unit 500 accurately detects the location information PI of the blood vessel BP, the blood flow measurement system 10 according to the present invention may focus its resources on measuring the blood flow velocity BV of the blood vessel BP. In this case, during the first driving interval OTI1, the first Doppler ultrasound transmission signal may be transmitted by focusing on a predetermined point included in the blood vessel BP using the first Doppler probe 200 driven by the first selection signal SE1, and the first Doppler ultrasound reception signal DUR1 reflected from the blood vessel BP and received by the first Doppler probe 200 may be received. In addition, during the second driving interval OTI2, the second Doppler ultrasound transmission signal may be transmitted by focusing on a predetermined point included in the blood vessel BP using the second Doppler probe 300 driven by the second selection signal SE2, and the second Doppler ultrasound reception signal DUR2 reflected from the blood vessel BP and received by the second Doppler probe 300 may be received. The blood flow measurement system 10 according to the present invention can calculate the blood flow velocity BV based on the first Doppler ultrasound reception signal DUR1 and the second Doppler ultrasound reception signal DUR2.

As can be seen from Equation illustrated in FIG. 11, when the first Doppler probe 200 and the second Doppler probe 300 are used, a first spectrogram corresponding to a first blood flow velocity and a second spectrogram corresponding to a second blood flow velocity over time may be generated without affecting the angle of incidence, and a velocity time integral (VTI) may be generated from the spectrogram. In one embodiment, the blood flow measurement system 10 according to the present invention may calculate the cardiac output based on the velocity time integral, the cross section area MZ, and a heart rate. Here, the cardiac output can be expressed as the product of the velocity time integral, the cross-sectional area MZ, and the heart rate.

The invention claimed is:

1. A blood flow measurement system, comprising: a guide imaging probe that includes a plurality of imaging ultrasound elements and is disposed along a first direction; a first Doppler probe that includes a plurality of first Doppler ultrasound elements and is disposed on one side of the guide imaging probe along a second direction corresponding to a direction perpendicular to the first direction; a second Doppler probe that includes a plurality of second Doppler ultrasound elements and is disposed on the other side of the guide imaging probe along a third direction corresponding to the direction perpendicular to the first direction; a processor configured to provide a control signal to control the guide imaging probe, the first Doppler probe, and the second Doppler probe; and a processor configured to detect location information of a blood vessel included in an object based on an image ultrasound reception signal, wherein the guide imaging probe transmits a first ultrasound signal to the object based on a first control signal received from the processor configured to provide the control signal, and the guide imaging probe receives the image ultrasound reception signal reflected from the object; and the guide imaging probe transmits a second ultrasound signal to the object based on a second control signal received from the processor configured to provide the control signal, wherein the first Doppler probe receives a first Doppler ultrasound reception signal and the second the second Doppler probe receives a second Doppler ultrasound reception signal reflected from the object.

2. The blood flow measurement system of claim 1, wherein the processor configured to detect location information of a blood vessel further includes a processor configured to measure a cross-sectional area corresponding to an area of a cross section of the blood vessel according to the location information of the blood vessel and a cross-section guide line formed in a depth direction of the ultrasound image.

3. The blood flow measurement system of claim 1, further comprising: a processor configured to calculate a blood flow velocity based on the first Doppler ultrasound reception signal received by the first Doppler probe and the second Doppler ultrasound reception signal received by the second Doppler probe.

4. The blood flow measurement system of claim 1, wherein the processor configured to provide the control signal further includes a processor configured to selectively drives the first Doppler probe and the second Doppler probe based on a selection signal.

5. The blood flow measurement system of claim 4, wherein the processor configured to selectively drives the first Doppler probe and the second Doppler probe sequentially and alternatively drives the first Doppler probe and the second Doppler probe at driving intervals corresponding to a predetermined constant time interval.

6. The blood flow measurement system of claim 5, wherein the blood flow measurement system operates in a plurality of operation modes, and when the processor configured to detect location information of the blood vessel detects the location information of the blood vessel, in a first operation mode among the plurality of operation modes, the processor configured to provide the control signal sequentially increases a transmission interval corresponding to an interval at which the transmitted ultrasound signal is transmitted.

7. The blood flow measurement system of claim 6, wherein when the processor configured to detect location information of the blood vessel detects the location information of the blood vessel, in a second operation mode among the plurality of operation modes, the processor configured to provide the control signal drives the first Doppler probe and the second Doppler probe to sequentially and alternatively transmit a first Doppler ultrasound transmission signal and a second Doppler ultrasound transmission signal to the blood vessel included in the object.

8. The blood flow measurement system of claim 3, wherein the processor configured to calculate the blood flow velocity calculates the blood flow velocity based on a first Doppler ultrasound reception signal received by the first Doppler probe by the first Doppler ultrasound transmission signal reflected from the blood vessel and a second Doppler ultrasound reception signal received by the second Doppler probe by the second Doppler ultrasound transmission signal reflected from the blood vessel.

9. The blood flow measurement system of claim 1, wherein after the first Doppler probe and the second Doppler probe transmit ultrasound signals to the object based on a third control signal received from the processor configured to provide the control signal, the first Doppler probe and the second Doppler probe receive the Doppler ultrasound reception signal reflected from the object.

* * * * *